United States Patent
Akai et al.

(10) Patent No.: US 7,612,205 B2
(45) Date of Patent: Nov. 3, 2009

(54) CRYSTALS OF QUINOLINECARBOXYLIC ACID DERIVATIVE SOLVATE

(75) Inventors: Jun Akai, Kyoto (JP); Hiroshi Nishida, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 89 days.

(21) Appl. No.: 10/555,039

(22) PCT Filed: Apr. 28, 2004

(86) PCT No.: PCT/JP2004/006216

§ 371 (c)(1),
(2), (4) Date: Sep. 12, 2006

(87) PCT Pub. No.: WO2004/096815

PCT Pub. Date: Nov. 11, 2004

(65) Prior Publication Data

US 2007/0149540 A1    Jun. 28, 2007

(30) Foreign Application Priority Data

Apr. 30, 2003 (JP) ............................ 2003-124643
Jan. 13, 2004 (JP) ............................ 2004-006057

(51) Int. Cl.
*C07D 513/04* (2006.01)
*A61K 31/4961* (2006.01)

(52) U.S. Cl. .................. 544/361; 514/253.03

(58) Field of Classification Search ........................ None
See application file for complete search history.

(56) References Cited

U.S. PATENT DOCUMENTS 5,086,049 A * 2/1992 Kise et al. .............. 514/210.16

FOREIGN PATENT DOCUMENTS

JP    1-294680 A    11/1989

OTHER PUBLICATIONS

English Translation for Kakemi et al. Iyakuhin Kenkyo, vol. 28, No. 1, pp. 1-11 (1997).*
Kakemi, Kazuo et al.; "Chemical Structure, Physico-chemical Properties and Stability of Prulifloxacin"; Iyakuhin Kenkyu vol. 28, No. 1, Jan. 20, 1997, pp. 1-11; p. 4., 2.1 Kessho Takei no ko.

* cited by examiner

*Primary Examiner*—Emily Bernhardt
(74) *Attorney, Agent, or Firm*—Darby & Darby P.C.

(57) ABSTRACT

A main object is to provide a crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate (Compound B) which is an intermediate for producing preferentially the type III crystal of 6-fluoro-1-methyl-7-[4-(5-methyl-2-oxo-1,3-dioxolen-4-yl) methyl-1-piperazinyl]-4-oxo-4H-[1,3]-thiazeto[3,2-a] quinoline-3-carboxylic acid (Compound A). A crystal of Compound B can be preferentially precipitated by controlling the supersaturation concentration in crystalization using acetonitrile as a solvent. Subsequently, the type III crystal of Compound A can be produced by performing desolvation of the crystal.

5 Claims, 4 Drawing Sheets

CRYSTALS OF QUINOLINECARBOXYLIC ACID DERIVATIVE SOLVATE

CROSS-REFERENCE TO PRIOR APPLICATION

This is a U.S. national phase application under 35 U.S.C. §371 of International Patent Application No. PCT/JP2004/006216 filed Apr. 28, 2004, and claims the benefit of Japanese Patent Application No. 2003-124643 filed Apr. 30, 2003, and Application No. 2004-006057 filed Jan. 13, 2004 which are incorporated by reference herein. The International Application was published in Japanese on Nov. 11, 2004 as WO 2004/096815 A1 under PCT Article 21(2).

TECHNICAL FIELD

The present invention relates to a crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid (hereinafter referred to as Compound A) acetonitrile solvate (hereinafter referred to as Compound B), a method for producing the crystal of Compound B, and a method for producing the type III crystal of Compound A using the crystal of Compound B.

BACKGROUND ART

Compound A has an excellent antibacterial activity (see, for example, Patent Document 1) and has been placed on the market as a synthetic antibacterial agent. It is known that there are 3 types of crystal forms (type I, type II and type III) of Compound A, and they are designated as type I, type II and type III in descending order of melting temperature in the measurement by differential scanning calorimetry (hereinafter referred to as DSC) (see, for example, Non-patent Document 1). In addition, by considering the solubility, absorbability, therapeutic effect and the like of the respective crystal forms, the type III crystal thereof has been placed on the market (see, for example, Non-patent Document 1).

It is known that the type I, type II and type III crystals of Compound A are obtained by crystallization from acetonitrile, however, the conditions of crystallization thereof have not been known, and existence of Compound B have not been known either (see, for example, Non-patent Document 1).

Patent Document 1: JP-A-1-294680

Non-Patent Document 1: Kazuro Kakemi and others 7, "Chemical Structure, physicochemical properties and stability of Prulifloxacin", IYAKUHIN KENKYU, vol. 28(1), pp 1-11 (1997)

DISCLOSURE OF THE INVENTION

An object of the present invention is mainly to provide a raw material for producing the type III crystal of Compound A having an excellent pharmaceutical and pharmacological effect, and a method for producing the same.

So far, it was considered that the type III crystal of Compound A was obtained directly from an acetonitrile solution of Compound A as well as the type I and type II crystals. However, the present inventors found that the type III crystal is not directly obtained by recrystallization like the type I and type II crystals, but it is obtained by desolvation of a crystal of Compound B (see Experimental Examples 1 to 3 described later). The present inventors found that the crystal of Compound B is an important intermediate for producing a drug product (the type III crystal of Compound A).

In addition, the present inventors have made intensive studies on a method for preferentially precipitating the crystal of Compound B, and as a result, they found that the object is achieved by controlling the supersaturation concentration (see Experimental Example 1 described later).

That is, the present inventors found that the crystal of Compound B can be preferentially precipitated by controlling the supersaturation concentration in crystallization using acetonitrile as a solvent, and then, by performing desolvation of the crystal, the type III crystal of Compound A can be produced, thus the present invention has been completed.

The present invention includes, (1) a crystal of Compound B, which has diffraction peaks at least at 7.3°, 14.7°, 19.2° and 22.3° in the powder X-ray diffraction spectrum;

(2) a method for producing a crystal of Compound B, which comprises performing crystallization from an acetonitrile solution of Compound A by controlling its supersaturation concentration (g/100 g) to be from 2.15 to 2.36 at the time of occurrence of spontaneous nucleation;

(3) a method for producing a crystal of Compound B, which comprises performing crystallization from an acetonitrile solution of Compound A by controlling its supersaturation concentration (g/100 g) to be from 0.41 to 2.36 at the time of addition of a seed crystal; and (4) the production method described in (3), wherein the solution at the time of addition of the seed crystal has a temperature of 70° C. or lower.

In the present invention, the term "spontaneous nucleation" means crystal nucleus which occurs spontaneously when performing crystallization without using seed crystal.

In the present invention, the term "supersaturation concentration: Cx (g/100 g)" means the degree of supersaturation state and it is represented by the following formula.

$$Cx = C - Cs$$

Where, C (g/100 g) indicates the mass (in terms of the desolvate) of Compound B dissolved in 100 g of a solvent.

Cs (g/100 g) indicates the saturation solubility (in terms of the desolvate) of Compound B dissolved in 100 g of a solvent under the temperature at the time of occurrence of spontaneous nucleation or addition of seed crystal.

That is, the case of Cx>0 indicates that it is in a supersaturation state, and the case of Cx<0 indicates a state where it does not reach saturation.

In the present invention, the term "amount in terms of the desolvate" means the mass obtained by converting the mass of Compound B (solvate) into the mass of desolvate. For example, in the case of 502.5 g of Compound B, the amount in terms of the desolvate becomes 461.5 g.

In the present invention, the term "desolvation" means removal of solvent from a solvate. For instance, in the case where a solvent is water, conversion of a hydrate into an anhydrous form by removing water molecules can be mentioned as an example.

BEST MODE FOR CARRYING OUT THE INVENTION

Figure 1:
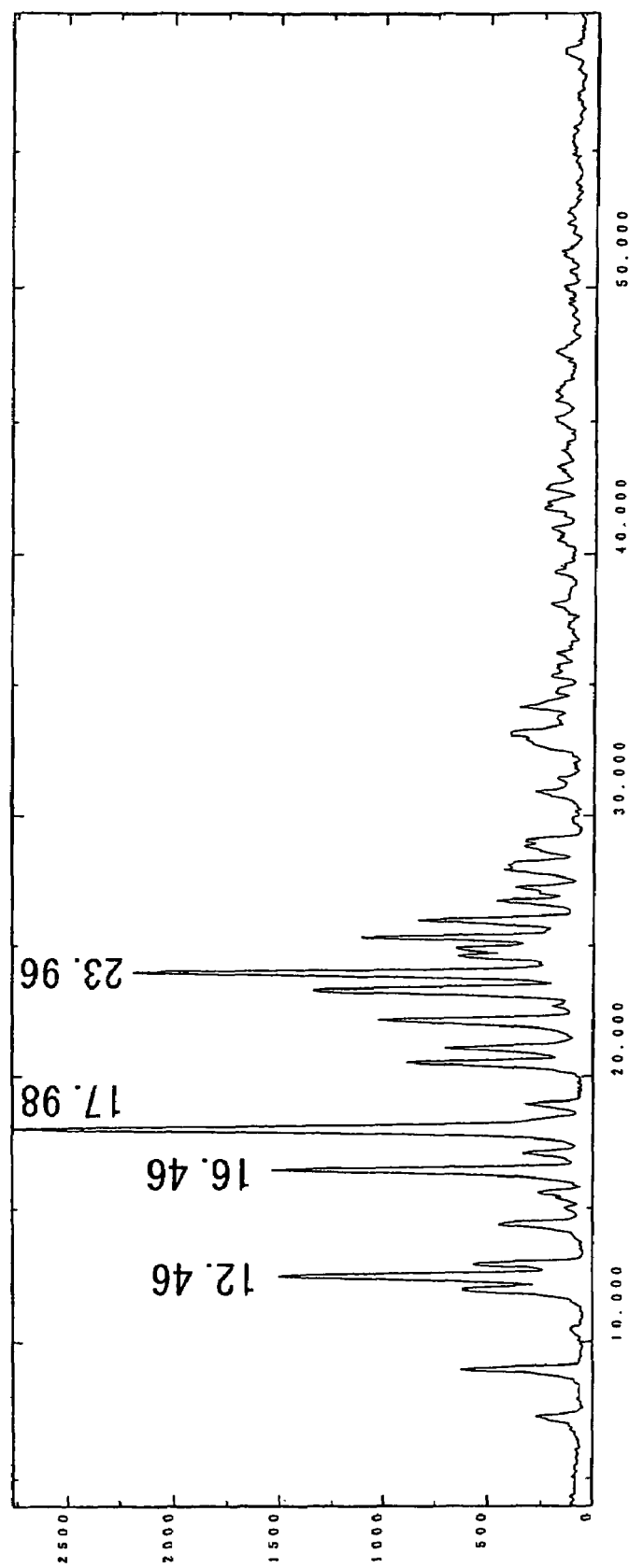
FIG. 1 shows a chart of powder X-ray diffraction spectrum of the type I crystal of Compound A. The vertical axis indicates the intensity (cps), and the horizontal axis indicates the diffraction angle (2θ±0.2°).

A crystal of Compound B can be produced by setting the supersaturation concentration (g/100 g) at the time of occurrence of spontaneous nucleation to be from 2.15 to 2.36, and performing crystallization from an acetonitrile solution of Compound A while suppressing formation of the type I or type II crystal of Compound A.

On the other hand, in the case where crystallization is performed under the condition of adding seed crystals, obtained crystals depends on the crystal form of the seed crystal. Therefore, the crystal of Compound B can be produced even under the condition where the supersaturation concentration (g/100 g) is from 0.41 to 2.36 in the crystallization by adding seed crystals compared with the crystallization by occurrence of spontaneous nucleation. It is preferred that seed crystals are added in an amount larger (not less than 0.004 g/100 g of solvent) than usual (less than 0.004 g/100 g of solvent). In the case where the amount of seed crystals is small, the added seed crystals become a stimulus and occurrence of new spontaneous nucleation is observed. However, in the case where the seed crystals are added in a large amount, growth of the added seed crystal takes priority, and occurrence of spontaneous nucleation is suppressed, whereby contamination of the type I or type II crystal of Compound A can be suppressed to the minimum level.

The crystal of Compound B is subjected to solvent mediated transformation, therefore, the temperature of a solution at the time of occurrence of spontaneous nucleation and at the time of addition of seed crystals is controlled to be 70° C or lower, preferably 67° C or lower, and more preferably 55° C or lower.

In the present invention, the term "solvent mediated transformation" means transformation of a crystal into another crystal form in the presence of a solvent. For example, it means that at a predetermined temperature, the crystal of Compound B is transformed into the type I crystal of Compound A in a solvent.

The type III crystal of Compound A can be produced by performing desolvation of the crystal of Compound B. Desolvation can be performed by drying the crystals of solvate according to a conventional method; however, it is preferred to perform it at 80° C. or lower under a reduced pressure. In addition, as described above, the type III crystal of Compound A is subjected to solvent mediated transformation, therefore the drying temperature is controlled to be 70° C. or lower, preferably 67° C. or lower, and more preferably 55° C. or lower.

More specifically, the crystal of Compound B can be produced, for example, as follows.

(1) Step of Dissolution

Compound A is dissolved in acetonitrile. The amounts of the used Compound A and acetonitrile are set so that a predetermined supersaturation concentration is obtained. It is preferred that the dissolution is performed by heating. There is no restriction on the heating temperature, however, it is preferably performed at a temperature around the boiling point of acetonitrile. In addition, it is preferred that this step is performed in a flow of an inert gas such as nitrogen or argon.

In order to remove insoluble substances, the solution may be subjected to filtration. In order to prevent crystal from forming during filtration, it is preferred to perform filtration by using a filter with a heating device under an increased pressure. In the case where formation of a crystals is observed in filtrate, the crystals can be dissolved again by reheating after filtration.

(2) Step of Cooling

The solution is cooled to precipitate a crystal out. It is necessary to control the temperature at which a crystal begins to precipitate, therefore, in the case where crystallization is performed without adding crystal seeds, attention is needed. There is no restriction on the cooling rate after a crystal is precipitated, however, cooling is performed preferably at a rate of about 0.04° C./min or faster, and more preferably at a rate of about 0.22° C./min or faster. There is no particular restriction on the cooling temperature (the temperature at the time of collecting precipitated crystals), however, it is preferably from 0 to 45° C., and more preferably from 0 to 25° C. There is no restriction on the holding time after reaching the cooling temperature, however, it is preferably 30 minutes or longer, and more preferably 90 minutes or longer. In addition, it is preferred that this step is performed under a stream of an inert gas such as nitrogen or argon.

(3) Step of Collection of Crystals

The precipitated crystals can be collected by a known method such as filtration or centrifugation, and can be dried. Drying of the precipitated crystals can be performed by a conventional method. In order to prevent solvent mediated transformation, the temperature during drying is set at 70° C. or lower, preferably 67° C. or lower, and more preferably 55° C. or lower. In addition, the crystal is liable to be desolvated, and formation of a desolvate is observed in some cases. In order to prevent desolvation, it is preferred to dry it at a ordinary temperature or lower under a reduced pressure. Incidentally, the crystal is used as a raw material of the type III crystal of Compound A, therefore, it may be used for a raw material of the type III crystal of Compound A described later without being particularly dried.

(4) Method for Producing the Type III Crystal of Compound A

The type III crystal of Compound A can be produced by performing desolvation of a crystal of Compound B according to a conventional method. There is no restriction on the drying condition as long as the solvent can be removed from the crystal of the solvate, however, drying is preferably performed at 80° C. or lower under a reduced pressure. In addition, in order to prevent solvent mediated transformation, drying is performed for several hours to several tens hours at a drying temperature of 70° C. or lower, preferably 67° C. or lower, and more preferably 55° C. or lower.

Hereunder, the present invention will be explained in more detail with reference to Reference Examples, Examples and Experimental Examples. It is needless to say that the present invention is not limited to the following Examples.

Incidentally, in this description, thermal analyses (DSC analysis and TG analysis) were carried out by using a heat flux differential scanning calorimeter DSC-50, a thermal gravimetric analyzer TGA-50, and a thermal analysis system TA-50, which are manufactured by Shimadzu, at a heating rate of 10° C./min, and powder X-ray diffraction was measured by using a powder X-ray diffractometer manufactured by Rigaku Denki Co. Incidentally, the measurement error of the apparatus is ±0.2°.

REFERENCE EXAMPLE 1

The type I crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid (Compound A)

Compound A was obtained according to the description of Patent Document 1. The compound (7.0 g) was dissolved by heating in 560 g of acetonitrile. The solution was gradually cooled, and at the time when the temperature of the solution became 25° C., 0.022 g of the type I crystal was added as seed crystal for allowing it to be precipitated, whereby 1.80 g of the type I crystal of Compound A was obtained. The crystal was subjected to DSC analysis, and as a result, the melting temperature (endothermic peak) was from 213 to 225° C. (degradation)

In Non-patent Document 1, crystal forms are designated as type I, type II and type III in descending order of melting temperature in DSC analysis. When comparing the results of DSC analysis of the crystals obtained in Reference Example 1, Reference Example 2 and Example 3, the crystal obtained in this Reference Example corresponded to the type I crystal of Compound A.

The data of the powder X-ray diffraction spectrum of the obtained crystal is shown in FIG. 1. The type I crystal of Compound A shows remarkable peaks at 12.5°, 16.5°, 18.0° and 24.0°.

REFERENCE EXAMPLE 2

The type II crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid (Compound A)

Compound A was obtained according to the description of Patent Document 1. The compound (14.4 g) was dissolved by heating in 560 g of acetonitrile. The solution was gradually cooled, and at the time when the temperature of the solution became 25° C., 0.02 g of the type II crystal was added as seed crystal for allowing it to be precipitated, whereby 10.8 g of the type II crystal of Compound A was obtained. The crystal was subjected to DSC analysis, and as a result, the melting temperature (endothermic peak) was from 179 to 189° C. (transformation to the type I crystal) and from 213 to 225° C. (degradation).

When comparing the results of DSC analysis of the crystals obtained in Reference Example 1, Reference Example 2 and Example 3, the crystal obtained in this Reference Example corresponded to the type II crystal of Compound A.

Figure 2:
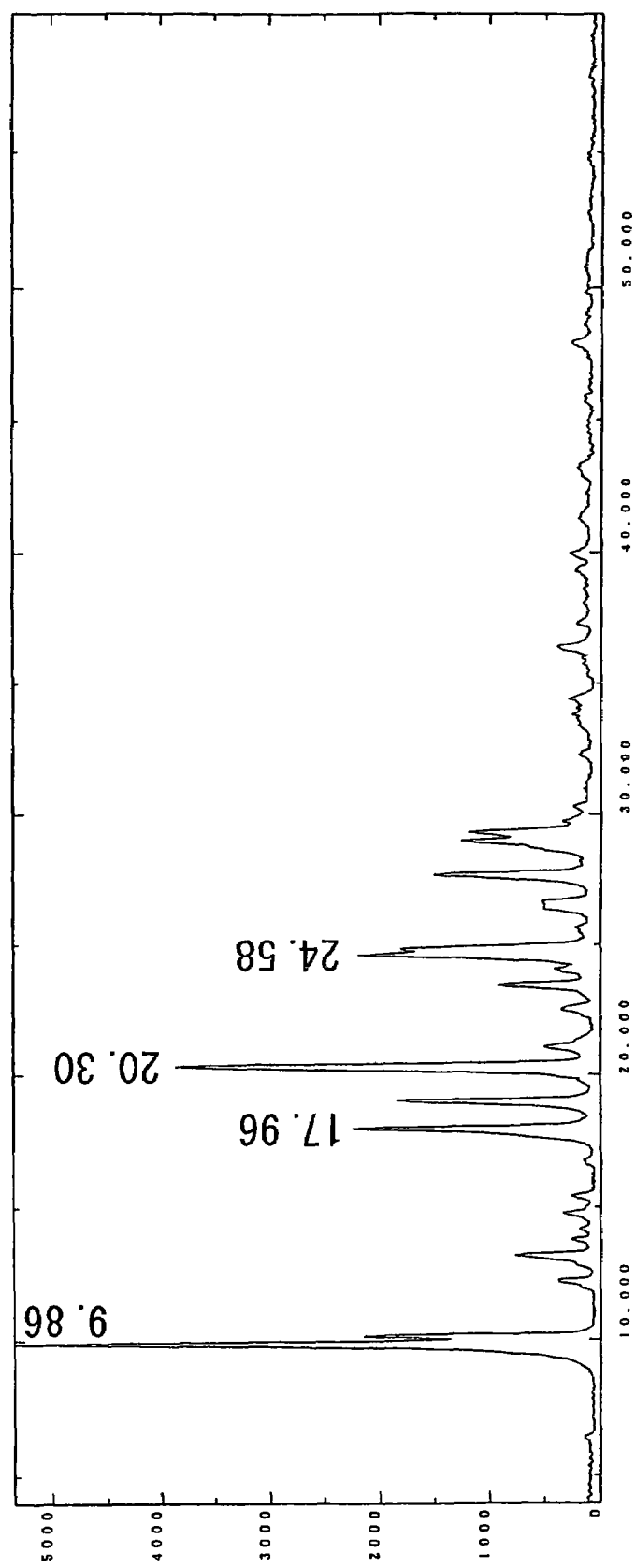
FIG. 2 shows a chart of powder X-ray diffraction spectrum of the type II crystal of Compound A. The vertical axis indicates the intensity (cps), and the horizontal axis indicates the diffraction angle (2θ±0.2°).

The data of the powder X-ray diffraction spectrum of the obtained crystal is shown in FIG. 2. The type II crystal of Compound A shows remarkable peaks at 9.9°, 18.0°, 20.3° and 24.6°.

EXAMPLE 1

A crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate (Compound B)

Compound A was obtained according to the description of Patent Document 1. The compound (15.0 g) was dissolved by heating in 560 g of acetonitrile, and crystallization was performed without adding seed crystals, whereby 11.99 g of the crystal of Compound B (in terms of the desolvate) was obtained. The crystal was subjected to DSC analysis, and as a result, the melting temperature (endothermic peak) was from ordinary temperature to 130° C. (desolvation), from 134 to 149° C. (transformation) and from 213 to 225° C. (degradation).

(1) From the results of DSC analysis and TG analysis, the reduced amount of the mass when desolvation occurred indicates that one molecule of acetonitrile is solvated by one molecule of Compound A. When the crystal after the mass was reduced was analyzed by powder X-ray diffraction, the same chart as that of the spectrum of the type III crystal of Compound A was obtained. (2) When powder X-ray diffraction analysis was carried out for the crystal obtained by keeping the type III crystal of Compound A in the saturated vapor of acetonitrile, the results coincided with the spectral data of the crystal of Example 1. In addition, (3) the crystal from which the adhering solvent was completely removed by thoroughly drying was analyzed by gas chromatography, and as a result, acetonitrile was detected. Further, (4) for crystallization, solvents other than acetonitrile were not used. From the results described above and the like, it was found that the crystal obtained in Example 1 is an acetonitrile solvate of Compound A (Compound B).

Figure 3:
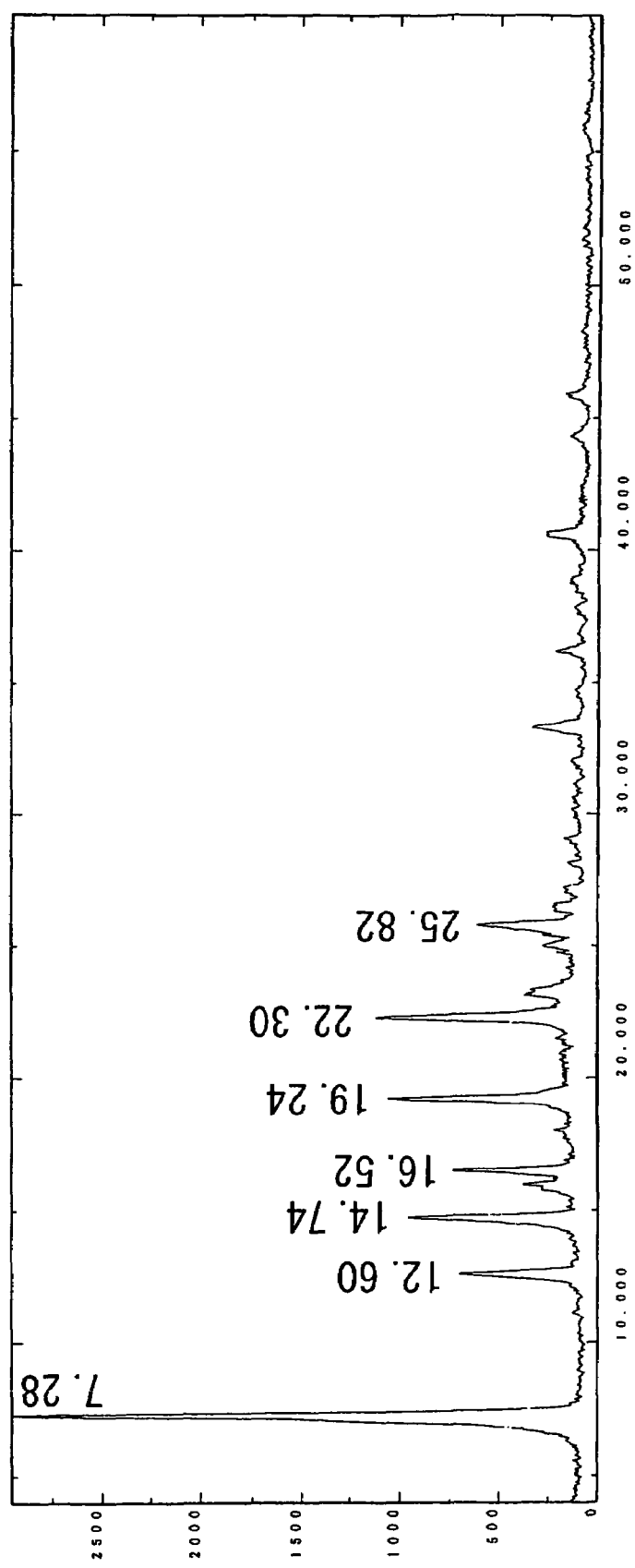
FIG. 3 shows a chart of powder X-ray diffraction spectrum of the crystal of Compound B. The vertical axis indicates the intensity (cps), and the horizontal axis indicates the diffraction angle (2θ±0.2°).

The data of the powder X-ray diffraction spectrum of the obtained crystal is shown in FIG. 3. The crystal of Compound B shows remarkable peaks at 7.3°, 12.6°, 14.7°, 16.5°, 19.2°, 22.3° and 25.8°. In particular, the peaks at 7.3°, 14.7°, 19.2° and 22.3° are characteristic.

EXAMPLE 2

A crystal of 6-fluoro-1-methyl-7-[4-(5-methyl-2-oxo-1,3-dioxolen-4-yl)-methyl-1-piperazinyl]-4-oxo-4H'-[1,3]thiazeto[3,2-a]quinoline-3-carboxylic acid acetonitrile solvate (Compound B)

Compound A was obtained according to the description of Patent Document 1. The compound (3.93 g) was dissolved by heating in 561.5 g of acetonitrile. The solution was gradually cooled, and at the time when the temperature of the solution became 25° C., 0.449 g of Compound B (in terms of the desolvate) was added as seed crystal for allowing it to be precipitated, whereby 0.70 g of the crystal of Compound B (in terms of the desolvate) was obtained. The physical values (measurement values of DSC and measurement values of X-ray diffraction) coincided with those of the crystal obtained in Example 1.

EXAMPLE 3

The type III crystal of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid (Compound A)

The crystal of Compound B (9.8 g) was dried for 24 hours at 50° C. under a reduced pressure (20 mmHg) for desolvation (with a yield of 9.0 g). The crystal was subjected to DSC analysis, and as a result, the melting temperature (endothermic peak) was from 134 to 149° C. (transformation) and from 213 to 225° C. (degradation).

When comparing the results of DSC analysis of the crystals obtained in Reference Example 1, Reference Example 2 and Example 3, the crystal obtained in this Reference Example corresponded to the type III crystal of Compound A.

Figure 4:
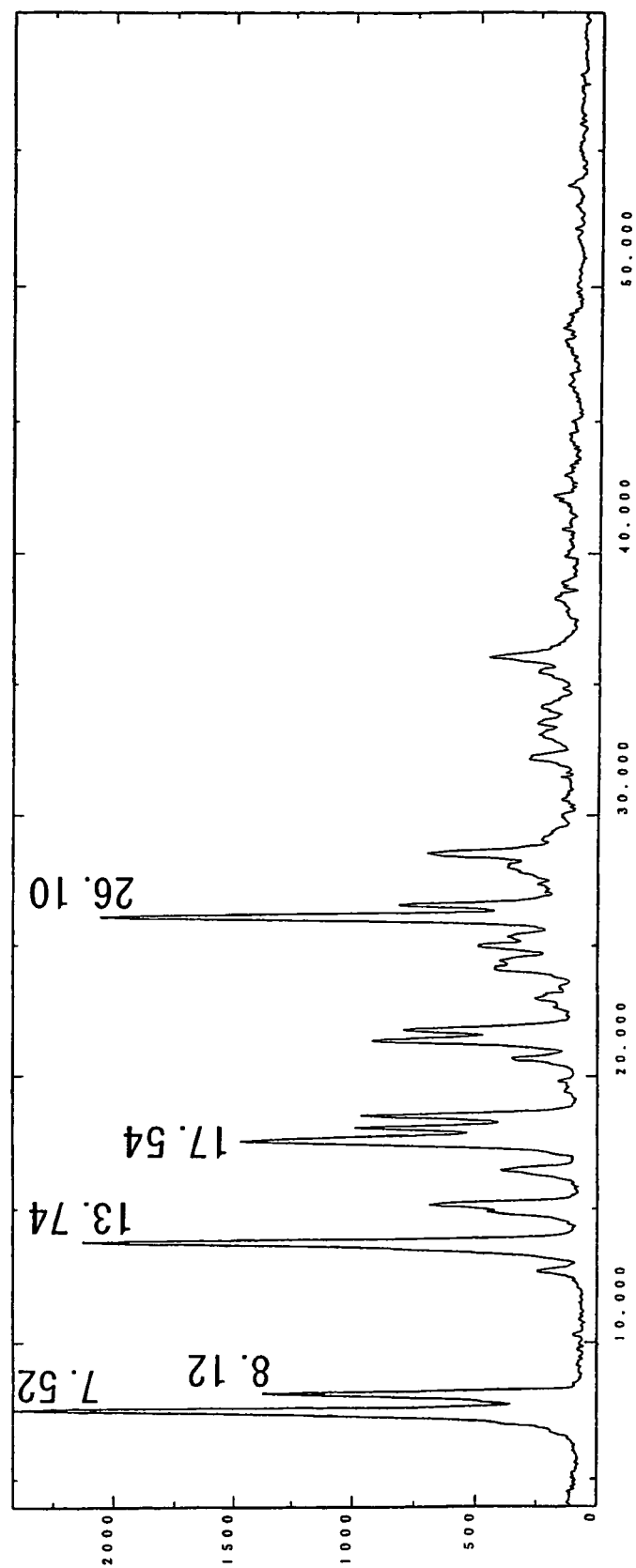
FIG. 4 shows a chart of powder X-ray diffraction spectrum of the type III crystal of Compound A. The vertical axis indicates the intensity (cps), and the horizontal axis indicates the diffraction angle (2θ±0.2°).

The obtained data of the powder X-ray diffraction spectra is shown in FIG. 4. The crystal of Compound B shows remarkable peaks at 7.5°, 8.1°, 13.7°, 17.5° and 26.1°. This chart of spectrum coincided with the X-ray diffraction spectra of the type III crystal of Compound A in Non-patent Document 1.

EXPERIMENTAL EXAMPLE 1

Effect of Supersaturation Concentration on Crystallization

A predetermined amount of Compound A was dissolved in a predetermined amount of acetonitrile, crystallization was carried out at various supersaturation concentrations, and the obtained crystals were analyzed with a powder X-ray diffractometer. The results are shown in Table 1.

found that the type III crystal of Compound A cannot be obtained directly by recrystallization.

In addition, in the case where seed crystals were not added, the crystal of Compound B was obtained when the supersaturation concentration (g 100 g) at the time of occurrence of spontaneous nucleation was from 2.15 to 2.36. However, when the supersaturation concentration was higher than the range, contamination of the type II crystal of Compound A was observed, and when it was lower than the range, contamination of the type I crystal of Compound A was observed.

In addition, in the case where the crystal of Compound B was added as seed crystal, the crystal of Compound B was obtained even when the supersaturation concentration (g/100 g) at the time of addition of seed crystals was from 0.41 to

TABLE 1

| Feed concentration (C) | Seed crystal | Temperature at the time of occurrence of spontaneous nucleation or addition of seed crystals (° C.) | Solubility at the time of occurrence of spontaneous nucleation or addition of seed crystals (Cs) | Supersaturation concentration (Cx) | Precipitated crystal form |
|---|---|---|---|---|---|
| 2.14 | Non | 25 | 0.29 | 1.85 | B + I |
| 2.44 | Non | 25 | 0.29 | 2.15 | B |
| 2.40 | Non | 17 | 0.19 | 2.21 | B |
| 2.40 | Non | 14.3 | 0.16 | 2.24 | B |
| 2.68 | Non | 27 | 0.32 | 2.36 | B |
| 3.66 | Non | 0 | 0.07 | 3.59 | II |
| 2.32 | III | 50 | 1.00 | 1.32 | B + I |
| 1.80 | III | 25 | 0.29 | 1.51 | B + I |
| 1.89 | III | 25 | 0.29 | 1.60 | B |
| 2.00 | III | 25 | 0.29 | 1.71 | B |
| 2.14 | III | 25 | 0.29 | 1.85 | B |
| 2.21 | III | 25 | 0.29 | 1.92 | B |
| 2.39 | III | 30 | 0.38 | 2.01 | B |
| 2.41 | III | 25 | 0.29 | 2.12 | B |
| 2.68 | III | 25 | 0.29 | 2.39 | B |
| 2.73 | III | 25 | 0.29 | 2.44 | B |
| 2.36 | B | 70 | 2.36 | 0.00 | B + I |
| 0.70 | B | 25 | 0.29 | 0.41 | B |
| 2.36 | B | 65 | 1.92 | 0.44 | B |
| 1.34 | B | 45 | 0.79 | 0.55 | B |
| 1.07 | B | 30 | 0.38 | 0.69 | B |
| 1.61 | B | 45 | 0.79 | 0.82 | B |
| 1.25 | B | 25 | 0.29 | 0.96 | B |
| 1.43 | B | 30 | 0.38 | 1.05 | B |
| 2.36 | B | 55 | 1.25 | 1.11 | B |
| 1.52 | B | 25 | 0.29 | 1.23 | B |
| 1.75 | B | 30 | 0.38 | 1.37 | B |
| 1.75 | B | 25 | 0.29 | 1.46 | B |
| 2.36 | B | 45 | 0.79 | 1.57 | B |
| 1.96 | B | 25 | 0.29 | 1.67 | B |
| 2.10 | B | 30 | 0.38 | 1.72 | B |
| 2.14 | B | 25 | 0.29 | 1.85 | B |
| 2.36 | B | 30 | 0.38 | 1.98 | B |
| 2.36 | B | 25 | 0.29 | 2.07 | B |
| 2.41 | B | 25 | 0.29 | 2.12 | B |

In Table 1, I indicates the type I crystal of Compound A, II indicates the type II crystal of Compound A, III indicates the type III crystal of Compound A, and B indicates the crystal of Compound B.

As shown in Table 1, the type III crystal of Compound A was not obtained by crystallization due to the occurrence of spontaneous nucleation nor even in the case where the type III crystal of Compound A was added as seed crystal. What was obtained was only the type I and the type II crystals of Compound A and the crystal of Compound B. Therefore, it was 2.12. This is considered that the crystal of Compound B was preferentially precipitated by suppressing the occurrence of another crystal nucleus (the type I crystal of Compound A) due to the addition of the seed crystals.

EXPERIMENTAL EXAMPLE 2

Desolvate of Crystal of Compound B

The crystal of Compound B was subjected to desolvation by drying at 80° C. for 24 hours under a reduced pressure, and the obtained crystal was measured with a powder X-ray diffractometer. As a result, the physical values of the obtained crystal coincided with those of the crystal obtained in Example 3. Therefore, it was found that the type III crystal of Compound A can be obtained by performing desolvation of the crystal of Compound B.

EXPERIMENTAL EXAMPLE 3

Investigation on Solvent for Crystallization (1) By adding 3 ml of a solvent to 50 mg of Compound A, it was investigated whether Compound A is dissolved or not.

(2) In order to investigate the stability of Compound A in a solvent, a 2-fold volume (the volume of a solvent (ml)/the weight of a dissolved substance (g)) of a solvent was added to Compound A, the mixture was maintained at 50° C. for 1000 minutes, and then the stability of the compound was investigated by high-performance liquid chromatography.

The results of the (1) described above are shown in the column of *1 of Table 2 and the results of the (2) described above are shown in the column of *2 of Table 2.

TABLE 2

| Solvent | Solubility (*1) | Chemical stability (*2) |
|---|---|---|
| acetonitrile | ○ | ○ |
| petroleum ether | X | — |
| ligroin | X | — |
| hexane | X | — |
| benzene | X | — |
| heptane | X | — |
| methylcyclohexane | X | — |
| toluene | X | — |
| xylene | X | — |
| p-cymene | X | — |
| carbon tetrachloride | X | — |
| chloroform | X | — |
| trichloroethylene | X | — |
| tetrachloroethylene | X | — |
| diisopropyl ether | X | — |
| tetrahydrofuran | X | — |
| dioxane | X | — |
| dibutyl ether | X | — |
| diphenyl ether | X | — |
| ethyl acetate | X | — |
| methyl acetate | X | — |
| isopropyl acetate | X | — |
| acetone | X | — |
| methyl ethyl ketone | X | — |
| ethanol | X | — |
| methanol | X | X |
| 2-propanol | X | — |
| isobutyl alcohol | X | — |
| 1-butanol | X | — |
| glycerin | X | — |
| cresol | X | — |
| formamide | X | — |
| pyridine | Δ | — |
| nitromethane | Δ | — |
| chloroacetonitrile | Δ | — |
| N,N-dimethylformamide | Δ | — |
| formic acid | Δ | X |
| acetic acid | Δ | X |
| aniline | Δ | X |
| 2-ethoxy ethanol | ○ | X |
| phenol | ○ | X |
| acetic anhydride | ○ | X |

In the column of *1 of Table 2, "○" indicates that in the case where a solvent has a boiling point of 130° C. or higher, the one in which Compound A is dissolved at 130° C., and in the case where a solvent has a boiling point of 130° C. or lower, the one in which Compound A is dissolved at the boiling point (solvents which are considered to be appropriate as a solvent for crystallization), "Δ" indicates that the one in which Compound A is dissolved at ordinary temperature (solvents which may be used as a solvent for crystallization), and "X" indicates that in the case where a solvent has a boiling point of 130° C. or higher, the one in which Compound A is not dissolved at 130° C., and in the case where a solvent has a boiling point of 130° C. or lower, the one in which Compound A is not dissolved at the boiling point (solvents which are not appropriate as a solvent for crystallization). In addition, in the column of *2 of Table 2, "○" indicates the one that did not have a peak other than that of Compound A (there is no degradation product), "X" indicates the one that had a peak other than that of Compound A (there is a degradation product), and "-" indicates untested.

As shown in the column of *1 of Table 2, as a solvent that may be able to be used for crystallization of Compound B, there were 7 kinds other than acetonitrile, namely, pyridine, nitromethane, chloroacetonitrile, N,N-dimethylformamide, formic acid, acetic acid and aniline. However, in the 3 kinds of solvents, namely, formic acid, acetic acid and aniline, a degradation product of Compound A was observed, therefore, the above-mentioned 3 kinds of solvents were not appropriate as a solvent for crystallization.

Accordingly, by using the other 4 kinds of solvents, a predetermined amount of Compound A was added to a predetermined amount of a solvent, dissolved by increasing the temperature to 78° C. or higher, and the mixture was cooled down to 25° C. Precipitated crystals were filtered, and measured with a powder X-ray diffractometer. The results are shown in Table 3.

TABLE 3

| | Feed amount | | |
| Solvent | Amount of dissolved substance (g) | Amount of solvent (mL) | Crystal form |
|---|---|---|---|
| pyridine | 4 | 67 | I |
| nitromethane | 3 | 50 | II |
| chloroacetonitrile | 1 | 5 | I |
| N,N-dimethylformamide | 6 | 50 | I |

In Table 3, I indicates the type I crystal of Compound A, II indicates the type II crystal of Compound A.

As shown in Table 3, with the investigated 4 kinds of solvents, a crystal other than the type I and the type II crystals of Compound A could not be obtained.

EXPERIMENTAL EXAMPLE 4

Investigation on Solvent Mediated Transformation

The crystal of Compound B was added to acetonitrile in an amount of not less than the supersaturation concentration at a predetermined temperature (in a state where not all the added crystals are dissolved and some crystals are present), stirred for 30 minutes, and then the crystal was filtered and measured with a powder X-ray diffractometer. The results are shown in Table 4.

TABLE 4

| Temperature (° C.) | Crystal form |
| --- | --- |
| 25 | Not changed |
| 40 | Not changed |
| 55 | Not changed |
| 67 | Not changed |
| 80 | Contaminated by the type I crystal of Compound A |

As shown in Table 4, it was found that at 67° C. or lower, transformation from the crystal of Compound B to another crystal was not observed, however, at 80° C., a part of the crystal of Compound B was transformed to the type I crystal of Compound A.

Therefore, it is considered that it is preferred to set the conditions of crystallization in such a manner that the crystal of Compound B is not allowed to exist in acetonitrile at not lower than 70° C. as much as possible.

INDUSTRIAL APPLICABILITY

The crystal of Compound B according to the present invention is an important intermediate for producing the type III crystal of Compound A. By producing the crystal of Compound B, the type III crystal of Compound A can be preferentially produced.

In addition, the crystal of Compound B can be produced by controlling the supersaturation concentration, therefore the production method of the same is an excellent method for providing a drug bulk substance (i.e., the type III crystal of Compound A) of high quality.

The invention claimed is:

1. A crystal form of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate, which has diffraction peaks at least at 7.3, 14.7, 19.2 and 22.3 in the powder X-ray diffraction spectrum.

2. A method for producing a crystal form of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate, which comprises performing crystallization from an acetonitrile solution of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid by controlling its supersaturation concentration (g/100 g) to be from 2.15 to 2.36 at the time of occurrence of spontaneous nucleation.

3. A method for producing a crystal form of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate, which comprises performing crystallization from an acetonitrile solution of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid by controlling its supersaturation concentration (g/100 g) to be from 0.41 to 2.36 at the time of addition of a seed crystal.

4. The method according to claim 3, wherein the solution at the time of addition of the seed crystal has a temperature of 70° C. or lower.

5. A method for producing the type III crystal form of 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid, which comprises desolvating crystalline 6-fluoro-1-methyl-7-[4-(5-methyl-2-oxo-1,3-dioxolen-4-yl)-methyl-1-piperazinyl]-4-oxo-4H-[1,3]thiazeto[3,2-a]quinoline-3-carboxylic acid acetonitrile solvate.

* * * * *